United States Patent [19]

Niwano

[11] 4,308,346
[45] Dec. 29, 1981

[54] SELECTIVE ISOLATION MEDIUM FOR CHOLERA VIBRIO

[75] Inventor: Kiyoshi Niwano, Tokyo, Japan

[73] Assignee: Nissui Seiyaku Co., Ltd., Tokyo, Japan

[21] Appl. No.: 125,190

[22] Filed: Feb. 27, 1980

[30] Foreign Application Priority Data

Sep. 25, 1979 [JP] Japan .................................. 54-122806

[51] Int. Cl.³ .............................................. C12Q 1/04
[52] U.S. Cl. ....................................... 435/34; 435/909
[58] Field of Search ....................... 435/34, 35, 36, 37, 435/38, 39, 40, 253, 254, 909

[56] References Cited

PUBLICATIONS

Edwin H. Lennette et al. (Editors), Manual of Clinical Microbiology, 2nd Ed. pp. 238-242 and 920; 1974.
C. H. Collins and Patricia M. Lyne, Microbiological Methods, pp. 133 and 142; 1976.
Sydney M. Finegold, M.D. et al., Bailey and Scott's Diagnostic Microbiology, 5th Ed. pp. 180-183; 1978.
R. E. Buchanan and N. E. Gibbons, Editors, Bergey's Manual of Determinative Bacteriology, 8th Ed., pp. 340-344; 1974.

*Primary Examiner*—Robert J. Warden
*Attorney, Agent, or Firm*—Oblon, Fisher, Spivak, McClelland & Maier

[57] ABSTRACT

The specification describes a selective isolation medium for cholera vibrio which comprises mannose, a sulfonphthalein colorant, polymyxin B, a surface active agent, and potassium tellurite. The above medium is excellent in both differentiability and in selectivity, and is particularly effective in detecting cholera bacteria from materials made available from environments or clinical inspection materials from patients on the way of the recovery, in which the number of cholera bacteria is small.

7 Claims, No Drawings

SELECTIVE ISOLATION MEDIUM FOR CHOLERA VIBRIO

This invention relates to a novel selective isolation medium for cholera vibrio.

The cholera vibrios or bacteria belong to the genus vibrio and when infected with cholera, one suffers from a disease accompanied by diarrhoea, nausea, and exsiccosis. Because of the epidemicity of the disease, it is frequently needed to detect cholera vibrios from patients or in environments such as waters, foods and the like.

The detection of cholera vibrios or bacteria has been heretofore made in various selective isolation media such as a TCBS (Thiosulfate Citrate Bile Salts) agar medium, a vibrio agar medium and the like.

However, since there are known a large number of nonagglutinable vibrios (NAG vibrios) belonging to the genus Vibrio which are similar to each another in physiological and biochemical properties, the isolation medium should have nature of allowing a selective growth of the cholera vibrios alone or a so-called selectivity, and nature of allowing a characteristic colony formation of cholera vibrios or a so-called differentiability.

The known media mentioned above are formulated so as to isolate and differentiate the bacteria belonging to the genus Vibrio from clinical materials such as faeses of patients, in which sucrose and a pH indicator are used as components for imparting the differentiability to the medium and the bile salts are used as components for imparting the selectivity.

However, the detection of cholera vibrios by these media has the following disadvantages:

(1) NAG vibrios other than cholera vibrio are allowed to grow up and thus the selectivity is low;
(2) Many NAG vibrious are able to decompose sucrose similarly to cholera vibrio and thus the differentiability becomes poor;
(3) The media serve to inhibit more or less the growth of cholera bacteria and thus a difficulty is encountered in detecting cholera bacteria, from materials made available from environments or materials from patients who are on the road to the recovery, i.e. materials which contain only a small number of cholera bacteria, or in detecting cholera bacteria whose growing ability has been weakened; and
(4) The growth colony becomes hard due to the presence of the bile salts which may lead to erroneous results in a subsequently conducted serum agglutination test.

Thus, the inspection of cholera bacteria by the known media was found to be complicate and incorrect and the contamination with cholera vibrios was often overlooked, especially, in environmental inspections.

Accordingly, an object of the present invention is to provide a selective isolation medium for cholera vibrio which is excellent both in differentiability and in selectivity.

Another object of this invention is to provide a selective isolation medium for cholera vibrio which is effective in detecting cholera bacteria from materials made available from environments or clinical inspection materials from patients on the way of the recovery, in which the number of cholera bacteria is small.

The above objects can be achieved by admixing mannose and sulfonphthalein colorant as differentiability-imparting components as well as polymyxin B, surface active agent and potassium tellurite as selectivity-imparting components.

That is, the present invention contemplates to provide a selective isolation medium for cholera vibrio, which comprises mannose, a sulfonphthalein colorant, polymyxin B, a surface active agent, and potassium tellurite.

Among surface active agents to be one component of the medium according to the present invention there are ampholytic surfactants such as, for example, sodium laurylsulfate, sodium heptadecylsulfate, and the like. The surface active agent is incorporated into the medium principally for the purspose of positively inhibiting the growth of gram positive bacteria. Polymyxin B serves to inhibit the growth of vibrio bacteria other than cholera bacteria and gram negative bacteria. On the other hand, potassium tellurite acts to inhibit the growth of bacteria which resist to the above-mentioned growth inhibitors.

The concentrations of these ingredients in the medium are preferably determined as follows: Polymyxin B is in the range of 100,000–200,000 U/l, the surface active agent is in the range of 0.009–0.25 w/v%, and potassium tellurite is in the range of 0.00008–0.00015 w/v%. The medium which comprises polymyxin B, the surface active agent and potassium tellurite in such concentrations as defined above gives no adverse influence on the growth of cholera bacteria, but inhibits the growth of substantially all other bacteria, and is thus very excellent in the selectivity.

Only a few types of bacteria can grow up in the medium containing the above-mentioned ingredients, among which there are almost no bacteria, except for cholera bacteria, which can decompose mannose into an acid. Accordingly, the presence of cholera bacteria can be easily inspected by the change of color in the medium when the sulfonphthalein colorant which changes in color by a change of pH is incorporated into the medium. The concentrations of these ingredients in the medium are preferably so determined that mannose is in the range above 1.5 w/v%, particularly 1.5–2.5 w/v%, and the sulfonphthalein colorant is in the range of 0.002–0.008 w/v%.

Among sulfonphthalein colorants usable for the medium of this invention, there are Bromothymol Blue, Thymol Blue, Cresol Red, Phenol Red and the like.

The medium according to this invention further comprises, aside from the ingredients discussed hereinabove, ordinarily employed nutrient sources such as peptone, meat extract, sodium chloride and the like, and agar powder.

The medium of the invention is prepared by dissolving the above ingredients in water under heating conditions, charging the thus-prepared solution into a container, and cooling it to a solid. In a preferred embodiment, the ingredients other than potassium tellurite are mixed and dried to give a dried powder and potassium tellurite is provided in another container. When used, the dried powder is dissolved in purified water under heating conditions, to which a dilute aqueous solution of potassium tellurite (preferably in a concentration of about 0.1%) is added, followed by charging it in a suitable container and cooling the same for solidification.

In order to detect cholera bacteria by using the medium of the present invention, a sample to be tested is applied onto the surface of the medium, cultured overnight at 37° C., and visually observed, upon which cholera bacteria, if any, are observed in the forms of yellow colonies.

The present invention will be particularly described by way of the following examples.

EXAMPLE 1

TABLE 1

| Composition of Selective Isolation Medium according to this Invention | |
|---|---|
| Meat extract powder | 5.0g |
| Polypeptone | 10.0g |
| Sodium chloride | 10.0g |
| D-Mannose | 20.0g |
| Agar powder | 15.0g |
| Polymyxin B | 180,000U |
| Sodium heptadecylsulfate | 0.1g |
| Cresol Red | 0.04g |
| Bromothymol Blue | 0.04g |
| Potassium tellurite | 1.0mg |
| Purified water | 1,000ml |

The above ingredients were dissolved in the purified water under heating conditions and every 20 ml of the thus-prepared solution was placed in a petri dish and cooled and solidified to prepare a medium.

EXAMPLE 2

Each of the medium prepared in Example 1, a TCBS (Thiosulfate Citrate Bile Salts) agar medium and a Vibrio agar medium was applied with a sewage incorporated with cholera bacteria (containing several to 1,000 cholera bacteria per mililiter of the sewage), cultured overnight at 37° C., and then visually observed. The compositions of the TCBS agar medium and Vibrio agar medium are shown in Tables 2 and 3 respectively. The results are shown in Table 4.

TABLE 2

| Composition of TCBS Agar Medium Per liter of aqueous medium: | |
|---|---|
| Yeast extract | 5.0g |
| Peptone | 10.0g |
| Sodium citrate | 10.0g |
| Sodium thiosulfate | 10.0g |
| Ox bile | 5.0g |
| Sodium cholate | 3.0g |
| Saccharose | 20.0g |
| Sodium chloride | 10.0g |
| Ferric citrate | 1.0g |
| Bromothymol Blue | 0.04g |
| Thymol Blue | 0.04g |
| Agar | 15.0g |
| pH: | about 8.6 |

TABLE 3

| Composition of Vibrio Agar Medium Per liter of aqueous medium: | |
|---|---|
| Yeast extract | 5.0g |
| Peptone | 5.0g |
| Saccharose | 12.5g |
| Sodium taurocholate | 5.0g |
| Sodium lauryl sulfate | 0.2g |
| Sodium citrate | 8.0g |
| Sodium thiosulfate | 8.5g |
| Disodium phosphate | 7.5g |
| Ferric citrate | 3.0g |
| Sodium chloride | 10.0g |
| Cresol Red | 0.02g |
| Water Blue | 0.2g |
| Agar | 15.0g |
| pH: | 8.5 ± 0.1 |

TABLE 4

| | | Test Results | | | | | |
|---|---|---|---|---|---|---|---|
| Specimen No. | The number of cholera bacteria per mililiter of sewage | Medium according to this invention | | TCBS agar medium | | Vibrio agar medium | |
| 1 | Several | + | (−) | − | (+) | − | (++) |
| 2 | Slightly over ten | ++ | (−) | − | (+) | + | (++) |
| 3 | One hundred | +++ | (−) | − | (+) | + | (++) |
| 4 | One thousand | +++ | (−) | + | (+) | ++ | (++) |

Note:
− Not observed.
+ 1–10 colonies were observed.
++ 11–99 colonies were observed.
+++ 100 or more colonies were observed.
The sign in the brackets ( ) indicates colonies of bacteria other than cholera bacteria.

EXAMPLE 3

One mililiter of the specimen No. 2 used in Example 2 was inoculated in 10 ml of the Monsur's peptone water (an enrichment medium for cholera bacteria) whose composition is shown in Table 5, followed by culturing at 37° C. for 8 hours. This medium was diluted to $10^2$, $10^3$, $10^4$, $10^5$ and $10^6$ times in volume. A predetermined amount of each of the dilutions was inoculated to the medium of the invention and the TCBS agar medium and the Vibrio agar medium whose compositions are respectively shown in Tables 1, 2 and 3, and the bacteria were cultured at 37° C. overnight to assess the state of their growth in a manner similar to Example 2. The results are shown in Table 6.

TABLE 5

| Composition of Monsur's Peptone Water | |
|---|---|
| Peptone | 10.0g |
| Sodium chloride | 10.0g |
| Sodium taurocholate | 5.0g |
| Sodium carbonate | 1.0g |
| Purified water | 1,000ml |
| pH: 9.0–9.2 | |

TABLE 6

| | Test Results | | | | | |
|---|---|---|---|---|---|---|
| Dilution | Medium according to this invention | | TCBS agar medium | | Vibrio agar medium | |
| $10^2$ | +++ | (−) | ++ | (−) | ++ | (+) |
| $10^3$ | +++ | (−) | + | (−) | + | (+) |
| $10^4$ | ++ | (−) | − | (−) | + | (+) |
| $10^5$ | + | (−) | − | (−) | − | (+) |
| $10^6$ | − | (−) | − | (−) | − | (+) |

The signs +++ ..... (+) have the same significance as defined in Example 2.

What is claimed is:

1. A selective isolation medium for cholera vibrio comprising mannose, a sulfonphthalein colorant, polymyxin B, a surface active agent, and potassium tellurite.

2. The selective isolation medium for cholera vibrio according to claim 1, comprising, on the basis of the total amount of the medium, 1.5–2.5 w/v% of mannose, 0.002–0.008 w/v% of the sulfonphtahlein colorant, 100,000–200,000 U/l of polymyxin B, 0.009–0.25 w/v% of the surface active agent, and 0.00008–0.00015 w/v% of potassium tellurite.

3. The selective isolation medium for cholera vibrio according to claim 1 or 2, wherein said sulfonphthalein colorant is Bromothymol Blue, Thymol Blue, Cresol Red or Phenol Red.

4. The selective isolation medium for cholera vibrio according to claim 1 or 2, wherein said surface active agent is an ampholytic surfactant.

5. The selective isolation medium for cholera vibrio according to claim 1 or 2, wherein said surface active agent is sodium laurylsulfate or sodium heptadecylsulfate.

6. The selective isolation medium for cholera vibrio according to claim 1, wherein said medium further comprises at least one additional nutrient source and agar powder.

7. The selective isolation medium for cholera vibrio according to claim 6, wherein said nutrient source is peptone, meat extract or sodium chloride.

* * * * *